US00PP13511P2

(12) United States Plant Patent
Carruth

(10) Patent No.: US PP13,511 P2
(45) Date of Patent: Jan. 28, 2003

(54) SHRUB ROSE PLANT NAMED 'WEKRERA'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/995,071

(22) Filed: Nov. 27, 2001

(51) Int. Cl.[7] ..... A01H 5/00
(52) U.S. Cl. ..... Plt./102
(58) Field of Search ..... Plt./102, 108

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Shrub rose suitable for garden decoration, having flowers of red and purple coloration.

1 Drawing Sheet

BOTANICAL CLASSIFICATION

*Rosa hybrida.*

VARIETY DENOMINATION

'WEKRERA'.

BACKGROUND OF THE INVENTION

This invention relates to a new and distinct variety of Shrub Rose. The varietal denomination of the new variety is 'WEKrera'. It has as its seed parent the variety known as 'MORedfar' (U.S. Plant Pat. No. 10,150) and as its pollen parent the variety known as 'FRYtrooper' (U.S. Plant Pat. No. 9,211).

SUMMARY OF THE INVENTION

Among the features which distinguish the new variety from other presently available and commercial rose cultivars known to the inventor are the following combination of characteristics: its very cupped flower form on the three-day-old flowers, its undulated petals, its red suffusion on the upper side of the stipules, its many seven-leaflet leaves and its light green foliage on the new shoots. The plant has a bushy very spreading to somewhat climbing growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKrera' may be asexually propagated by cuttings, budding or grafting.

COMPARISON WITH PARENTS

The new rose may be distinguished from its seed parent, 'MORedfar' by the following combination of characteristics: wheras 'WEKrera' produces medium size red flowers which fade to a magenta-blue coloration, the seed parent produces significantly smaller light red flowers which fade to a lighter pink coloration. 'MORedfar' bears small foliage on a small bush with slightly spreading growth habit, whereas the new variety bears significantly larger foliage on a significantly larger bush with very spreading to somewhat climbing growth habit.

The new variety may be distinguished from its pollen parent, 'FRYtrooper' by the following combination of characteristics: whereas 'FRYtrooper' bears dark red flowers with dark green leaves, 'WEKrera' bears flowers of lighter red and purple coloration with significantly lighter green foliage. The new variety has a bushy very spreading to somewhat climbing plant growing habit, whereas the pollen parent has a more compact and bushy growing habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety sometimes bears its flowers singly, usually in clusters of three to several per stem. Flowers may be borne in irregular rounded to somewhat pyramidal clusters on strong medium to long stems (about 52 to about 142 cm.). Outdoors, the plant blooms abundantly and nearly continously during the growing season. The flowers have a slight musk to apple-like fragrance.

BUD

The peduncle is about 1.2 to 3.1 cm. in length, of average caliper (about 0.1 to about 0.25 cm. in diameter), and usually erect. It is moderately smooth, with numerous stipitate glands and many hairs. Peduncle color is between 144B and 138C sometimes moderately suffused, especially on the side exposed to the sun, with between 183C and 187B.

Before the calyx breaks, the bud is about 0.7 to about 1.2 cm. in diameter at the widest point, about 0.7 to about 1.3 cm. in length, and ovoid to somewhat pointed in shape with a moderately conspicuous neck. The surface of the bud bears some foliaceous appendages and few stipitate glands, usually with slender entire foliaceous parts extending beyond the tip of the bud about ½ or more of its length. Bud color is between 144A and 138B sometimes moderately suffused, especially on the side exposed to the sun, with between 183B and 187B.

The sepals are about 1.4 to about 1.8 cm. in length and about 0.5 to about 0.7 cm. in width at the widest point. The outer surface of the sepal is between 144A and 138B sometimes moderately suffused, especially on the side exposed to the sun, with between 183B and 187B. The inner surface of the sepal is between 138C and 147D and covered with fine wooly tomentum; sepal margins are lined with many stipitate glands and hairs.

As the petals open (after the calyx breaks), the bud is about 1.1 to about 1.6 cm. in diameter at the widest point, about 1.5 to about 2.0 cm. in length, and moderately pointed to somewhat ovoid in form. The color of the under and upper surfaces of the newly opened petals is between 60A and 59B. On the under surface, at the point where the petal attaches, there is a moderately small zone of between 12C and 9C. On the upper surface, at the point where the petal attaches, there is a moderately small zone of between 13B and 14C.

BLOOM

When fully open, the bloom ranges from about 4.2 to about 6.3 cm. in diameter. Petalage is semi-double with about 8 to 13 petals and about 3 to 5 petaloids irregularly arranged. When partially open, the bloom form is moderately cupped, and the petals are loosely cupped to moderately undulated with petal edges sometimes moderately reflexed inward and sometimes slightly reflexed outward. When fully open, the bloom form is somewhat flat to slightly cupped, and the petals are somewhat cupped to slightly flat and undulated with petal edges sometimes moderately reflexed inward and sometimes slightly reflexed outward. On the three-day old flowers, the bloom form is very cupped and the petals are cupped to moderately undulated with petal edges sometimes moderately reflexed inward and sometimes slightly reflexed outward.

PETALS

The substance of the petals is moderately heavy and of medium to moderately thick thickness, with upper surfaces moderately satiny to somewhat velvety and under surfaces slightly shiny to matte. The outer petals are broadly obovate to somewhat oval in shape with moderately rounded to somewhat retuse apices. The inner petals are more broadly obovate in shape with moderately rounded to somewhat retuse apices. The petals are about 1.8 to about 2.5 cm. in length and about 1.6 to about 2.4 cm. in width at the widest point. Petal margins are mostly entire to sometimes slightly crenate.

NEWLY OPENED FLOWER

The under and upper surface color of the outer, intermediate and inner petals is between 53A and 60A. On the under surface, at the point where the petal attaches, there is a moderately small zone of between 9D and 8C. On the upper surface, at the point where the petal attaches, there is a moderately small zone of between 12B and 13C.

The general tonality of the newly opened flower is between 53A and 60A.

THREE-DAY-OLD FLOWER

The under surface color of the outer and inner petals is between 63B and 64B. The upper surface color of the outer and inner petals is between 61B and 64B. On the under and upper surfaces color, at the point where the petal attaches, there is a somewhat large zone of between 11D and 155B.

The general tonality of the three-day old flower is between 61B and 64B.

On the spent bloom, the petals usually drop off cleanly.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (average about 68) and are arranged regularly about the pistils; a few are mixed with petaloids. The filaments are of medium to long length (about 0.3 to about 0.7 cm.), most with anthers. Filaments are between 13B and 14B in color. The anthers are moderately small for the class and all open approximately at the same time. Anther color is between 21B and 22A when immature and between 163C and 165B at maturity. Pollen is moderately abundant.

FEMALE REPRODUCTIVE ORGANS

Pistils vary in number (average about 29). The styles are moderately even, somewhat short in length (about 9.3 to about 0.5 cm.), average to somewhat heavy in caliper, and loosely bunched to slightly columnar. Stigma is near 2C. Style color is near 1D. Ovaries are usually all enclosed in the calyx.

Hips have not been observed on this variety when grown in Upland, Calif.

FOLIAGE

The compound leaves are usually comprised of three to seven leaflets and are borne abundantly. The seven-leaflet leaves are about 7.2 to about 12.8 cm. in length and about 5.2 to about 7.3 cm. in width at the widest point, somewhat heavy to slightly crisp in texture, and moderately glossy in finish. The terminal leaflets are about 3.2 to about 5.0 cm. in length and about 1.9 to about 3.0 cm. in width at the widest point, shaped bradly oval to somewhat ovate with very acute apices and moderately rounded to slightly cordate bases. Their margins are usually simply serrate.

The upper surface color of the mature leaf is between 147A and 137B. The under surface color of the mature leaf is between 146B and 148C. The upper and under surface color of the young leaf is between 144A and 146C.

The rachis is somewhat light in caliper and moderately smooth. The upper side is very lightly grooved with many hairs and very few stipitate glands on the edges of the grooves. The under side of the rachis is mostly smooth with many hairs and very few small prickles. The rachis color is between 144B and 145A sometimes lightly suffused with between 187B and 183B.

The stipules are about 0.9 to about 1.9 cm. in length and of medium width (about 0.4 to about 0.6 cm.) with medium to somewhat long straight points that usually turn out at an angle of more than 45 degrees and sometimes recurve toward the stem. The stipules color is between 146C and 144B usually moderately suffused with between 187B and 183B.

The petiole is about 0.7 to about 1.6 cm. in length and about 0.1 to about 0.2 cm in diameter at the widest point. The petiole color is between 146C and 144B sometimes lightly suffused with between 187B and 183B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a bushy very spreading to somewhat climbing medium height growing habit (about 122 to about 140 cm. in height and about 157 to about 176 cm. spread at the widest point), with very full branching. It displays very vigorous growth and the canes are moderately light to medium in caliper for the class.

The color of the major stems is between 146C and 144A. They bear some large prickles that are about 0.5 to about 0.8 cm. in length. The large prickles are almost straight and angled moderately downward with a moderately short to medium length somewhat narrow oval base; prickle color is between 166B and 166C. The major stem bears no small prickles.

The color of the branches is between 144A and 146C sometimes moderately suffused with between 183C and 187B. They bear few large prickles which are of similar size and shape to the large prickles on the major stems; prickle color is between 160B and 161B. The branches bear many small prickles of similar shape and coloration.

The color of the new shoots is between 144B and 146D sometimes heavily suffused with between 183C and 187B. They bear few large prickles which are of similar size and shape to the large prickles on the major stems; prickle color is near 160B usually heavily suffused with between 183C and 187B. The new shoots bear many small prickles of similar shape and coloration.

I claim:

1. A new and distinct Shrub rose plant of the variety substantially as described and illustrated herein.

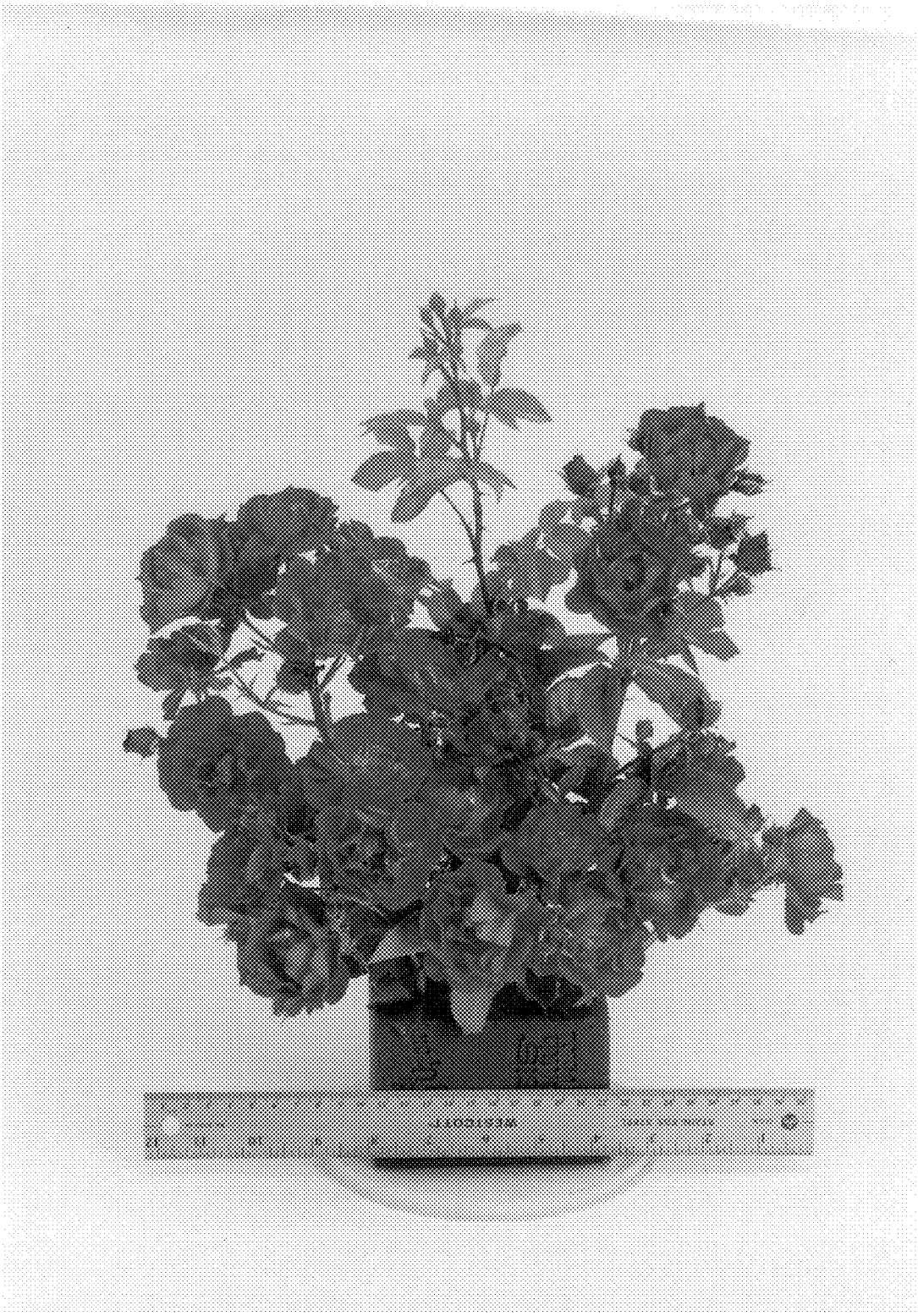

* * * * *